United States Patent [19]

Finidori

[11] Patent Number: 6,056,944
[45] Date of Patent: May 2, 2000

[54] PHARMACEUTICAL COMPOSITIONS FOR ORAL USE INCLUDING AN NSAID AND CERAMIDES

[75] Inventor: Claudine Finidori, Montrouge, France

[73] Assignee: Synthelabo, Le Plessis Robinson, France

[21] Appl. No.: 09/077,790

[22] PCT Filed: Dec. 4, 1996

[86] PCT No.: PCT/FR96/01925

§ 371 Date: Jun. 8, 1998

§ 102(e) Date: Jun. 8, 1998

[87] PCT Pub. No.: WO97/20572

PCT Pub. Date: Jun. 12, 1997

[30] Foreign Application Priority Data

Dec. 6, 1995 [FR] France .................. 95 14392

[51] Int. Cl.[7] .............. A61K 7/16; A61K 7/22; A61K 7/26
[52] U.S. Cl. .................. 424/49; 424/54; 424/58
[58] Field of Search .................. 424/49–58

[56] References Cited

U.S. PATENT DOCUMENTS

| | | | |
|---|---|---|---|
| 5,032,384 | 7/1991 | Yeh et al. | 424/49 |
| 5,190,981 | 3/1993 | Wechter | 514/900 |
| 5,331,000 | 7/1994 | Young et al. | 514/570 |
| 5,342,976 | 8/1994 | Bowser et al. | 554/36 |
| 5,352,387 | 10/1994 | Rahman et al. | 252/548 |
| 5,411,948 | 5/1995 | Lingwood et al. | 514/78 |
| 5,443,840 | 8/1995 | Murancais et al. | 424/450 |
| 5,565,207 | 10/1996 | Kashibuchi et al. | 424/401 |
| 5,624,673 | 4/1997 | Bonte et al. | 424/195.1 |
| 5,626,838 | 5/1997 | Cavanaugh | 424/54 |
| 5,626,868 | 5/1997 | Murancais et al | 424/450 |
| 5,639,734 | 6/1997 | Esko et al. | 514/23 |
| 5,679,360 | 10/1997 | de Lacharriere et al. | 424/401 |
| 5,730,998 | 3/1998 | de Lacharriere et al. | 424/443 |
| 5,741,518 | 4/1998 | Ribier et al. | 424/450 |
| 5,807,541 | 9/1998 | Aberg et al. | 424/52 |
| 5,817,646 | 10/1998 | Gossioux | 514/78 |
| 5,851,556 | 12/1998 | Breton et al. | 424/639 |
| 5,866,158 | 2/1999 | Ribier et al. | 424/450 |

FOREIGN PATENT DOCUMENTS

| | | |
|---|---|---|
| 249561 | 5/1992 | European Pat. Off. . |
| 717 998 | 6/1996 | European Pat. Off. . |
| 4447287 | 11/1996 | Germany . |
| 93 05752 | 4/1993 | WIPO . |
| 93 09805 | 5/1993 | WIPO . |
| WO 93/09805 | 5/1993 | WIPO . |
| 94 12467 | 6/1994 | WIPO . |
| 97 20572 | 6/1997 | WIPO . |

OTHER PUBLICATIONS

Svennerholm "Destination and schematic structure of Gangliosides and Allied Glycosphingolipids" In Progress in Brain Research 101 Sympos. 83 Biological Function of Gangliosides XI–XIV, 1994.

Matsuzaki Chem. Pharm.Bull. 41(3);575–579 (Ceramics Ketoproton), 1993.

Elias et al WO/PCT 9817253 (Ceramides, NSAIDS), Apr. 1998.

CEVC WO/PCT 9817255 (Ceramides, NSAIDS), Apr. 1998.

Primary Examiner—Shep K. Rose
Attorney, Agent, or Firm—Jacobson, Price, Holman & Stern, PLLC

[57] ABSTRACT

Polar lipid composition of plant origin for conveying an active agent and/or making it penetrate into a target cell, the composition being characterized in that it is comprised of an injectable, intra-articular, topical or ingestable aqueous emulsion of a polar lipid mixture rich in phospholipids, in glycolipids and in ceramides, having a composition which is substantially similar to that of the polar lipids constituents of lipid cytomembranes of cells and obtained from a plant compound such as cereal flour or an extract such as bran or lipids extracted from cereals by means of chlorinated solvants.

8 Claims, No Drawings

PHARMACEUTICAL COMPOSITIONS FOR ORAL USE INCLUDING AN NSAID AND CERAMIDES

This is a 371 of PCT/FR96/01925 filed Dec. 4, 1996 based on priority of FRANCE 9514392 filed Dec. 6, 1995.

The present invention relates to pharmaceutical compositions for oral use which include a nonsteroidal antiinflammatory agent (NSAI) and to their use for preventing and treating periodontal disorders.

NSAIs are not widely used for preventing and treating periodontal disorders, that is disorders which affect the periodontium, such as gingivites or periodontites. The periodontium consists of support tissues for the tooth. It is mainly composed of gingiva, ligament, alveolar bone and cementum. The limited use of NSAIs for preventing and treating periodontal disorders can be explained by the fact that, in general, compositions for oral use which include NSAIs are not sufficiently effective. Thus, while a relatively high dose of NSAI is required if this type of composition is to be adequately effective, such high doses of NSAI are, in general, poorly tolerated by the periodontium.

The present invention therefore proposes novel compositions for oral use, which compositions include NSAIs and exhibit an appreciably improved efficacy while at the same time being well tolerated by the periodontium. These compositions are useful for preventing and treating periodontal disorders.

The invention thus consists of a pharmaceutical composition for oral use, which includes a nonsteroidal antiinflammatory agent (NSAI) and ceramides.

The applicant has observed that ceramides enable the NSAIs to be vectorized, that is they improve the availability of the NSAIs at the site of action. Thus, the ceramides, alone or in combination with other compounds described below, form a vectorizing base.

Ceramides are lipids which generally comprise from 14 to 34 carbon atoms, more generally from 17 to 23 carbon atoms. They are constituents of the plasma membranes of animal cells. They are also present in plants in the form of lipid mixtures which include, in particular, phospholipids such as lecithins in addition to the ceramides.

Ceramide derivatives are also known which comprise one or more monosaccharides which are attached to the constitutive carbon chain of the ceramides. These monosaccharides can consist of glucose, galactose, mannose, fucose, glucosamine or galactosamine. These ceramide derivatives which include one or more monosaccharides are an integral part of the present invention. For the sake of simplicity, and unless otherwise indicated, the term ceramide is understood, within the context of the present invention, as meaning both ceramides per se and said ceramide derivatives.

As indicated above, the ceramides can be used alone or in the form of mixtures which can, in particular, include, apart from the ceramides, other lipids such as phospholipids as well as, where appropriate, proteins.

Those mixtures which can be used within the context of the present invention, as well as the process for preparing them, are described in international application PCT/FR92/01048.

The ceramides of the invention are preferably of plant origin.

A pharmaceutical composition according to the invention can include from 0.005 to 5% by weight, preferably from 0.2 to 2% by weight, of ceramides.

The ceramides employed can be in the form of an aqueous emulsion whose oily phase consists, at least in part, of ceramides and, where appropriate, of other lipids.

The NSAI is advantageously selected from benzydamine, ketoprofen or ketoprofen lysine. A pharmaceutical composition according to the invention can include from 0.005 to 10% by weight, preferably from 0.25 to 2.5% by weight, of NSAI.

A pharmaceutical composition for oral use according to the invention can be in the form of dentifrices, mouthwashes or gels. Apart from the NSAI and the ceramides, the pharmaceutical composition can include at least one other excipient such as acrylic acid polymers, carboxyvinyl polymers, silicas, propylene glycol, polyethylene glycols, fatty acid esters, hard paraffin, ethanol, isopropanol, diethanolamine, triethanolamine, glycerol, hydroxyethylcellulose and carboxymethylcellulose (CMC), for gels; calcium carbonate or phosphate, hydrated aluminas or silicas, carboxymethylcellulose, carragheenates, alginates, sodium lauryl sulfate or sodium lauryl sarcosinate, polyglycerolated dodecanediol, glycerol, sorbitol and propylene glycol for dentifrices; alcohols such as glycerol and ethanol for mouthwashes.

The pharmaceutical compositions can also include, as the case may be and in the usual manner, preservatives, emulsifiers, buffer salts, sweeteners, fragrances and dyes.

The pharmaceutical compositions according to the invention can be prepared in a manner which is conventional for the skilled person.

As shown in Examples 1 to 3 below, ceramides on the one hand exhibit an inhibitory activity against human leucocyte enzyme, which enzyme is responsible for the destruction of connective tissue during inflammatory reactions, and on the other hand induce an anti-inflammatory effect which is greater than that of NSAI when used alone at the same dose. The pharmaceutical compositions of the present invention can therefore be used in the prevention and treatment of periodontal disorders such as gingivites or periodontites.

The following examples illustrate the invention. They were all carried out using plant ceramides which were extracted from wheat flour and which are marketed by INOCOSM Laboratories. These plant ceramides contain 80% glycosylceramides as well as 10% gliadin and 10% apolar lipids.

EXAMPLE 1

An investigation was carried out into the role of ceramides in preventing the destruction of connective tissue which takes place, in particular, in periodontal disorders.

Periodontal disorders are characterized by gingival inflammation.

During inflammatory processes, the proteolytic enzymes which are released can, if they are not inactivated by protease inhibitors, bring about tissue destruction. In particular, elastase has been demonstrated to have a role in degrading the gingival extracellular matrix during an inflammation.

Tests were therefore carried out in vitro and ex vivo in order to investigate the effects exerted by the ceramides on the leucocyte elastase.

The in-vitro test consisted in incubating human leucocyte elastase with plant ceramides for 5 min, which is the time required for forming the enzyme/inhibitor complex, and then with a synthetic substrate, i.e. N-methoxysuccinyl—Ala—Ala—Pro—Val-p-nitroanilide.

The enzyme brings about hydrolysis of the synthetic substrate, giving rise to a colored product, i.e. p-nitroaniline, the appearance of which is monitored by its absorbance at 410 nm. The rate at which the product of the reaction appears is measured in the presence or absence of plant ceramides and using different substrate and ceramide concentrations. The ratio between the initial velocities enables the percentage inhibition of the enzyme to be determined in terms of the ceramide concentration in the reaction medium.

The results obtained showed that ceramides are inhibitors of leucocyte elastase and that the ceramide concentration which produces a 50% inhibition is 32.7 µg/ml.

The ex-vivo study was carried out on human skin biopsies and rat gingival biopsies. Thus, rat gingivas and human gingivas possess a structure which is comparable to that of the skin, being made up of preelastic fibers in the superficial part of the extracellular matrix and of mature elastic fibers deeper down, with collagen fibers being the main constituent of the connective tissue.

The biopsies, in 8 mm-thick sections, were divided into 4 groups, which were subjected to the following treatments:

treatment 1: incubation in 200 µl of tris-HCl buffer, pH 8, at 37° C. for 12 hours (negative control group).

treatment 2: incubation with leucocyte elastase alone at 37° C. for 12 hours (control group).

treatment 3: action of plant ceramides alone (200 µl of 1% solution), then 2 washes with PBS and finally incubation with human leucocyte elastase (200 µl of a 10 µg/ml solution in the case of the skin and of a 2 µg/ml solution in the case of the gingivas). This treatment makes it possible to study the formation of a substrate/ceramide complex.

treatment 4: mixture of plant ceramides and human leucocyte elastase for 30 min, then incubation of the mixture with the sections at 37° C. for 12 hours. This treatment makes it possible to study the formation of an enzyme/ceramide complex.

The sections are then rinsed, fixed with 70% alcohol and stained, either with catechin-fuchsin in order to visualize the elastic fibers, or with Sirius red in order to visualize the collagen fibers.

The determination, by computerized image analysis, of the volumetric fraction occupied by the fibers enables the percentage inhibition of the enzyme to be measured.

Following treatment 2, the leucocyte elastase was observed to have caused substantial destruction of the mature elastic fibers.

The results obtained following treatment 4 demonstrated greater than 90% protection of the elastic fibers as a result of the inhibitory action of the plant ceramides on the enzyme.

The collagen fibers were also observed to have been protected following treatments 3 and 4, indicating that the ceramides interact at one and the same time with the collagen fibers and with the human leucocyte elastase.

EXAMPLE 2

The anti-inflammatory effect of the compositions of the invention was studied by determining their anti-free radical potency in relation to the superoxide anion in vitro.

Thus, it is known that the polymorphonuclear cells which are activated during the anti-inflammatory process produce free radicals.

It is also known that inflammation is accompanied by the activation of enzymes, such as cyclooxygenase, which activate free radical formation.

The anti-free radical action of an anti-inflammatory composition is therefore a good indication of its anti-inflammatory potency.

The anti-free radical potency of compositions according to the invention was determined by measuring the decrease in the rate of reduction of cytochrome C when the product to be studied was added to the reaction medium.

The superoxide anion is generated by the action of xanthine oxidase on xanthine and results, in the absence of a molecule which is capable of capturing it, in the reduction of the cytochrome C.

The appearance of the reduced cytochrome C is followed in a spectrophotometer at 550 nm.

Emulsions which included an NSAI and ceramides were prepared for carrying out these tests.

These emulsions, the composition of which was as follows:

| plant ceramides | 0.5 g |
| lecithin | 0.5 g |
| gum xanthan | 0.3 g |
| NSAI | 0.5 g |
| water | qs for 100.0 g, | were prepared by adding, while stirring vigorously, the ceramides, the lecithin and the NSAI and then cooling while stirring, followed by autoclaving.

They were then diluted ½ and ¼ in order to obtain NSAI concentrations of 2.5 mg/ml and 1.25 mg/ml.

Compositions of this nature, containing ketoprofen, ketoprofen lysine and benzydamine, respectively, were tested and the results were compared with the results which were obtained with solutions which contained the same constituents apart from the ceramides.

The results which were obtained showed that the anti-free radical protection provided by the compositions which included the ceramides increased, depending on the NSAI and its concentration, from 6 to 22% as compared with the compositions which did not include any ceramides.

EXAMPLE 3

Tests of anti-inflammatory activity were also carried out in vivo.

These tests consist in inducing inflammation of the adult rat paw and monitoring the development of the edema by measuring the volume of the paw.

The experimental conditions were as follows: rats, weighing from 200 to 220 g, were treated by gavage, 18 hours and 1 hour before administering the inflammatory agent, with the NSAI product to be studied, which was or was not combined with ceramides and which was administered in a volume of 0.5 ml. Control groups were given an 0.9% solution of sodium chloride.

The inflammatory reaction is induced by subcutaneously injecting 0.1 ml of a suspension of carragheenin in physiological saline. The volume of the paw is measured, using a mercury plethysmograph, before the inflammation starts, 30 minutes after it has started, and then every hour up to the 6th hour, and then finally 24 hours afterwards. The changes in volume are measured in cm on a graduated scale.

The tests were carried out with ketoprofen lysine, which was administered at 1 and 3 mg/kg and which was or was not combined with 0.5% of ceramides, and with ketoprofen, which was administered at 1 mg/kg and which was or was not combined with 1% of ceramides.

The results which were obtained showed that the ketoprofen lysine, when administered at 1 and 3 mg/kg and combined with ceramides, induces an anti-inflammatory effect, from the 3-hour stage onwards, which is significant as compared with the control and which persists up to 6 hours.

The ketoprofen lysine, when administered at 1 mg/kg and combined with ceramides, has an anti-inflammatory effect which is significantly greater than that produced by the same compound when administered at 1 and 3 mg/kg but not combined with ceramides (reduction, at the 4-hour stage, of approximately 60% as compared with the groups which were treated with the compound administered at 1 and 3 mg/kg but not combined with ceramides).

When administered at 1 mg/kg, and whether combined or not with ceramides, ketoprofen induces, from 4 hours onwards, an anti-inflammatory effect which is significant as compared with the control, with this effect persisting up to 5 hours.

When administered at 1 mg/kg, ketoprofen which is combined with ceramides has an effect which is greater than that of ketoprofen which is administered at the same dose but which is not combined with ceramides (reduction, at the 5-hour stage, of approximately 15% as compared with the group treated with the compound which was not combined with ceramides).

In the examples which follow, the % values are % by weight.

EXAMPLE 4: Dentifrice

| | |
|---|---|
| ketoprofen | 2.00 g |
| ceramides | 2.00 g |
| fluoride (NaF or KF) | from 1000 to 5000 ppm |
| silicas | 18.00 g |
| 70% sorbitol | 25.00 g |
| carboxymethylcellulose | 1.50 g |
| sodium lauryl sulfate | 0.75 g |
| polyglycerolated dodecanediol | 0.75 g |
| parabens* | 0.30 g |
| mint flavor | 1.20 g |
| water | qs for 100.00 g |

*50/50 (weight/weight) mixture of methyl para-hydroxybenzoate and propyl para-hydroxybenzoate.

EXAMPLE 5: Dentifrice

| | |
|---|---|
| benzydamine | 1.00 g |
| ceramides | 0.50 g |
| silicas | 15.00 g |
| glycerol | 20.00 g |
| sodium carragheenate | 2.00 g |
| sodium lauryl sulfate | 1.50 g |
| parabens* | 0.30 g |
| mint flavor | 1.20 g |
| water | qs for 100.00 g |

*50/50 (weight/weight) mixture of methyl para-hydroxybenzoate and propyl para-hydroxybenzoate.

EXAMPLE 6: Mouthwash

| | |
|---|---|
| ketoprofen | 1.00 g |
| ceramides | 1.50 g |
| alcohol | 5.00 g |
| dye | 0.30 g |
| mint flavor | 0.20 g |
| sodium saccharinate | 0.20 g |
| water | qs for 100.00 ml |

EXAMPLE 7: Mouthwash

| | |
|---|---|
| benzydamine | 0.50 g |
| ceramides | 0.50 g |
| glycerol | 2.00 g |
| alcohol | 5.00 g |
| Tween 80 | 0.50 g |
| sodium saccharinate | 0.15 g |
| flavor | 0.12 g |
| water | qs for 100.00 ml |

EXAMPLE 8: Oral Gel

| | |
|---|---|
| ketoprofen | 3.00 g |
| ceramides | 2.00 g |
| glycerol | 20.00 g |
| hydroxyethylcellulose | 5.00 g |
| flavor | 0.30 g |
| sodium saccharinate | 0.30 g |
| water | qs for 100.00 g |

EXAMPLE 9: Oral Gel

| | |
|---|---|
| benzydamine | 2.00 g |
| ceramides | 1.50 g |
| 95° alcohol | 40.00 g |
| glycerol | 10.00 g |
| carboxymethylcellulose | 5.00 g |
| flavor | 0.30 g |
| water | qs for 100.00 g |

What is claimed is:

1. A toothpaste, mouthwash or gel composition to be applied topically onto the periodontium, for preventing and/or treating periodontal diseases, said composition comprising from 0.005 to 5% by weight of a nonsteroidal anti-inflammatory agent (NSAI) and from 0.005 to 10% by weight of an agent for enhancing the anti-inflammatory activity of NSAI, said enhancing agent comprising ceramides which contain 80% glycosylceramides.

2. The composition of claim 1, wherein the NSAI agent is benzydamine, ketoprofen or ketoprofen lysine.

3. The composition of claim 1, wherein the ceramides are in the form of an aqueous emulsion.

4. The composition of claim 1, wherein the ceramides are of plant origin.

5. The composition of claim 1, wherein the composition comprises from 0.25 to 2.5% by weight of NSAI.

6. The composition of claim 1, wherein the composition comprises from 0.2 to 2% by weight of ceramides.

7. A method for preventing and/or treating periodontal diseases, said method comprising the step of administrating topically onto the periodontium a toothpaste, mouthwash or gel composition, said composition comprising from 0.005% to 5% by weight of a nonsteroidal anti-inflammatory agent (NSAI) and from 0.005 to 10% by weight of an agent for enhancing the anti-inflammatory activity of NSAI, said agent comprising ceramides which contain 80% glycosylceramides.

8. The composition of claim 1, wherein the NSAI agent is benzydamine and the composition is in the form of a mouthwash.

* * * * *